United States Patent
Schilling (10) Patent No.: US 8,915,874 B2
(45) Date of Patent: Dec. 23, 2014

(54) ADJUSTING DEVICE FOR A JOINT MECHANISM

(75) Inventor: Matthias Schilling, Weißenborn-Lüderode (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 13/991,038

(22) PCT Filed: Nov. 29, 2011

(86) PCT No.: PCT/EP2011/005974
§ 371 (c)(1),
(2), (4) Date: May 31, 2013

(87) PCT Pub. No.: WO2012/072231
PCT Pub. Date: Jun. 7, 2012

(65) Prior Publication Data
US 2013/0253393 A1   Sep. 26, 2013

(30) Foreign Application Priority Data

Dec. 3, 2010   (DE) .......................... 10 2010 053 176

(51) Int. Cl.
*A61F 5/00* (2006.01)
*A61F 5/01* (2006.01)

(52) U.S. Cl.
CPC ........... *A61F 5/01* (2013.01); *A61F 2005/0158* (2013.01); *A61F 2005/0167* (2013.01); *A61F 5/0102* (2013.01)
USPC ....................... 602/16; 602/5; 602/26; 602/27

(58) Field of Classification Search
CPC . A61F 5/01012; A61F 5/0585; A61F 5/0123; A61F 5/0125; A61F 5/0111; A61F 5/0113; A61F 5/0193
USPC ................................ 602/5, 16, 20, 22, 23–29
See application file for complete search history.

(56) References Cited

U.S. PATENT DOCUMENTS 5,358,469 A   10/1994   Patchel et al.
7,534,220 B2   5/2009   Cormier et al.
(Continued)

FOREIGN PATENT DOCUMENTS

DE   10311187 A1   10/2004
DE   202008015764 A1   3/2009
DE   102008027639 A1   12/2009

OTHER PUBLICATIONS

PCT International Search Report for PCT International Patent Application No. PCT/EP2011/005974, mailed Mar. 5, 2012.

*Primary Examiner* — Kim M Lewis
(74) *Attorney, Agent, or Firm* — Holland & Hart (57) ABSTRACT

An adjusting device having a first element and a second element movably mounted with respect thereto, wherein the first element has at least one latching device, and wherein at least one locking element coupled to an actuating element is movably disposed on the second element and can be moved out of a release position out of engagement with the latching device into a locking position in engagement with the latching device. The adjusting device has a simple construction which functions reliably and enables rapid adjustment of the stop position. The actuating element has at least one actuating magnet, which is associated with a locking magnet coupled to the locking element and the locking element moves into the release position and/or locking position and/or out of the release position and/or locking position.

20 Claims, 9 Drawing Sheets

(56) References Cited

U.S. PATENT DOCUMENTS

| | | | |
|---|---|---|---|
| 7,602,270 B2 * | 10/2009 | Krause | 335/220 |
| 2002/0169402 A1 | 11/2002 | Hatton et al. | |
| 2005/0039762 A1 | 2/2005 | Lidolt et al. | |
| 2005/0082843 A1 * | 4/2005 | Edgar | 292/216 |

* cited by examiner

ADJUSTING DEVICE FOR A JOINT MECHANISM

TECHNICAL FIELD

The invention relates to an adjusting device having a first element and a second element, which is mounted so as to be displaceable with respect thereto, the first element has at least one latching device, at least one locking element, which is coupled with an actuating element, is arranged so as to be displaceable on the second element, said locking element being movable out of a release position out of engagement with the latching device into a locking position in engagement with the latching device. Such an adjusting device can be used in a sensible manner as a joint mechanism in particular in the case of ortheses or prostheses with pivotable joint elements, in particular such a joint mechanism can be fastened on an orthesis in order to establish the mobility of the joint in a targeted manner.

BACKGROUND

U.S. Pat. No. 5,358,469 describes an orthesis having a joint mechanism on which a rail is arranged on a first joint element and a rail is arranged on a second joint element. The securing to a limb, in particular to a leg, is effected by means of the rails. The joint mechanism has a common rotational axis about which the two joint elements pivot in relation to one another. The joint mechanism has associated therewith a spring which can bring about a preloading in the direction of flexion and/or extension in order to support a movement or to counteract it. The pivoting movement is restricted by means of a pin-shaped stop with a housing in which spring-loaded locking pins are arranged. Holes in which the locking pins engage are provided in a housing in order to define the extent of the pivoting movement. In order to adjust the stop position, the retaining pins are pressed into the housing and displaced to the desired bore.

U.S. Pat. No. 7,534,220 B2 describes an orthesis having two rails which are mounted so as to be rotatable side by side. A lower leg rail and an upper rail are arranged on a joint mechanism. Each rail is preferably fastened on the joint mechanism by means of rivets. An extension, which is produced from a rigid material, for example steel, and has a row of adjusting holes spaced apart from one another, can be fastened on each rail. As soon as the desired length adjustment has been performed, it is fixed by means of a screw-in button or a locking lever. Elevations, which indicate in a haptic manner the correct alignment of the rails with respect to one another, are provided in order to facilitate the aligning of the adjusting holes with respect to the locking elements.

The design of such a joint mechanism is costly, the adjustment of the stop position requires fine motor abilities and the structure is susceptible to contamination and water ingress.

SUMMARY

It is the object of the present invention to provide an adjusting device which is constructed in a simple manner, functions reliably and makes it possible for a stop position or bearing bolt to be adjusted in a rapid manner.

The object is achieved as claimed in the invention by an adjusting device with the features of the main claim, advantageous developments and further developments of the invention are shown in the sub-claims, the description and the figures.

The adjusting device as claimed in the invention, having a first element and a second element, which is mounted so as to be displaceable, e.g. pivotable or slidable, with respect thereto, the first element having at least one latching device and at least one locking element, which is coupled with an actuating element, being arranged so as to be displaceable on the second element, said locking element being movable out of a release position out of engagement with the latching device into a locking position in engagement with the latching device, provides that the actuating element has at least one actuating magnet which is associated with a locking magnet which is coupled with the locking element and the locking element moves into the release position and/or locking position and/or out of the release position and/or locking position. By means of the development of the actuating element with an actuating magnet, it is possible to bring about in an active manner a locking or unlocking of an adjusting device or an adjusting of a locking element. The magnet does not exert a mechanical load on the locking element such that mechanical wear, as when tension springs and compression springs are used, cannot be produced. Using the actuating magnet, rapid changeover between a release position and a locking position is possible, over and above this there does not have to be any direct mechanical operative connection between the actuating element and the locking element such that, for example, an application in encapsulated assemblies is also possible. In this case, the actuating element with the actuating magnet is able to move the locking element by means of the locking magnet in an active manner into the locking position and back out again. Likewise, active take-up of the release position or removal out of the release position can be effected. In principle, it is also possible for a preferred position of the locking element to be present, for example, by means of the force of gravity or preloading by means of an elastomer element such that preferably a locking position is assumed. The actuating element then operates the locking element only in the direction of the release position and then enables conscious adjustment of the position of the locking element. Once a magnetic interaction has ceased, the locking element then latches automatically into the latching device. A reverse method of operation is also possible such that the release position is present as the preferred position whilst a locking position is assumed in an active manner by means of the actuating element. The locking element can secure the elements together. As an alternative to this or in addition to it, it is possible for the locking element to be realized as a thrust block on which components can be mounted and the position of which is adjustable.

The actuating element is preferably mounted so as to be displaceable or pivotable on the adjusting device, in particular on the second element. In particular, the actuating element can be arranged on the upper surface of the adjusting device on the second element such that it is easy to reach and in addition there is sufficient space for actuation.

The locking element can be realized as a slidingly mounted pin and the latching device can be realized as a recess in which the locking element engages when it has been displaced into the locking position. It is also possible for the locking element to be realized in a manner corresponding to an alternatively formed latching device and, as a result, it is possible to lock the two elements with respect to one another in a positive locking manner. The locking element can be realized, for example, as a clamp or clasp, whilst the latching device is realized as a projection or as gearing in which the locking element engages in positive locking manner.

The actuating magnet can have its magnetic polarity reversed if it is realized as an electric magnet, as an alternative to this the actuating magnet can be mounted so as to be able to have its magnetic polarity reversed, in particular can be rotatably mounted such that different poles act on the locking magnet and depending on the position one time an attracting and one time a repelling effect is realized. Frequently, the release position is brought about with an attracting action and the displacement into a locking position is brought about with a repelling action.

At least one holding magnet, which holds the actuating element in the respective position on the second element and does not have the task primarily of attracting or repelling the locking magnet, can be arranged on the actuating element. In principle, it is possible for several magnets, for example two or three magnets, to be arranged in the actuating element, one of which serves as the actuating magnet and the other magnet or the other magnets serve as holding magnets. The holding magnet prevents the actuating element from being unintentionally displaced out of the position once it has been adjusted.

The locking element can be arranged on the second element between two holding magnets which are aligned with opposite poles, a further holding magnet with the same magnetic polarity being arranged next to the holding magnet with a magnetic polarity which deviates from the locking magnet. In the case of such an arrangement with four magnets in a row, it is possible for always two holding magnets arranged on the second element to be active and over and above this for the locking element to be displaced into the desired position. The locking magnet and a further holding magnet, in this case, have the same magnetic polarity, two holding magnets arranged next to the locking magnet have a reverse magnetic polarity. Actuation of the locking element and at the same time secure fixing with two pairs of holding magnets in both positions can be effected by means of the magnetic polarity in pairs and an arrangement of holding magnets in the actuating element.

It is equally possible for the second element to be magnetizable at least in part, for example to have a magnetizable wall such that adhesion to a magnetizable surface is possible at least in the region of the securing of the actuating element on the second element. The locking element can be effected by an interaction between the locking magnet and the actuating magnets, which at the same time are also holding magnets, right through the magnetizable surface.

The locking element can be mounted in a spring-loaded manner in the second element such that a preferred position is present when the magnetic forces fall away. Likewise, where the housing is developed in a magnetizable manner, the spring force can bring about an at least partial compensation of the holding force by means of the locking magnet.

The two elements can be mounted as joint elements about a common pivot axis, the elements being arranged in a common pivot plane and being able to be in a flat, disc-shaped or sleeve-shaped form. The elements can be mounted in a spring-preloaded manner in relation to one another in at least one pivot direction in order to support the human joint during bending or stretching. The adjusting device itself, in this case, does not have to have a carrying function, rather it can be realized as a modular attachment part on an orthesis or prosthesis such that spring preloading can be realized in the direction of flexion or the direction of extension and can consequently support the respective movement.

Along with complete locking of the adjusting device and consequently also where applicable of the prosthesis or orthesis, it is possible for the locking device to fix the movement boundaries of the elements which are displaceable toward one another, e.g. of the joint, that is for the respective maximum angular positions to be fixed in the direction of extension and the direction of flexion, proceeding from a start position. The locking device then locks a movement beyond a certain angle or a certain stretch and only permits restricted pivoting or displacement between the boundaries which are fixed by the locking device or several locking devices in the adjusting device.

Two actuating magnets with different magnetic polarity can be arranged in the actuating element in order no bring about the different positions of the locking element, that is a displacement out of the release position into the locking position and, vice versa, out of the locking position into the release position.

BRIEF DESCRIPTION OF THE DRAWINGS

Exemplary embodiments of the invention are explained in more detail below by way of the attached figures. Identical references designate identical components. In the figures.

DETAILED DESCRIPTION

Figure 1:
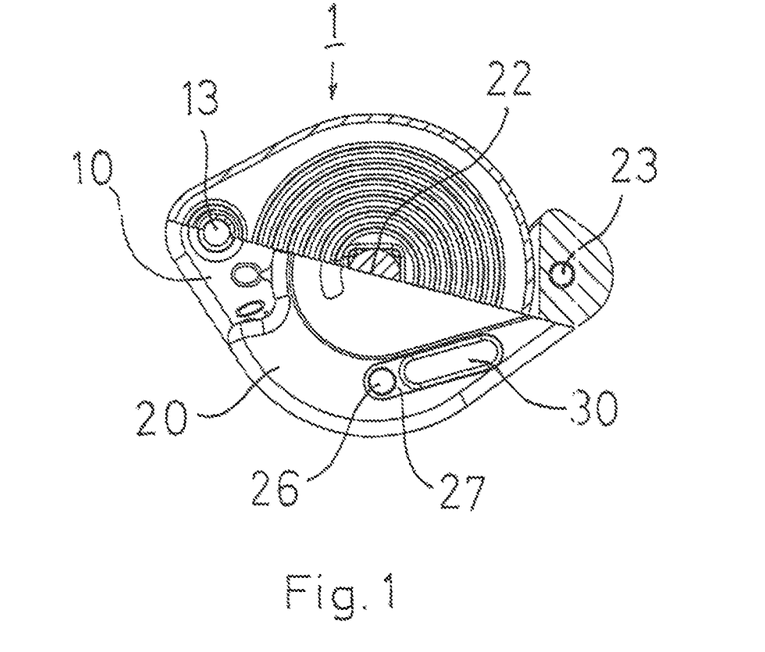
FIG. 1 shows a schematic, part-sectional top view of an adjusting device.

FIG. 1 shows a perspective representation of an adjusting device 1 having a first element 10 and a second element 20. A bore 13 is realized on the first element 10, by means of which bore a securing for example on a first orthesis rail can be effected. The second element 20 is mounted on the first element 10 so as to be pivotable about a pivot axis 22. Also present and provided on the second element 20 is an accommodating bore 23 for securing on a second orthesis rail which can be connected to the first rail by means of a separate element. The pivot axis 22 preferably extends through the pivot axis of the adjusting device, to which the two orthosis rails are connected so as to be pivotable together.

On its upper surface, the second element 20 has an actuating element 30 which is mounted so as to be slidable in a guide 27. A holding magnet 26 can be seen inside the guide, by means of which holding magnet the actuating element 30 is held in the adjusted position when the actuating element 30 is slid to the left in the guide 27. The method of operation of the holding magnet 26 and of the adjusting device is described in more detail further below.

Figure 1A:
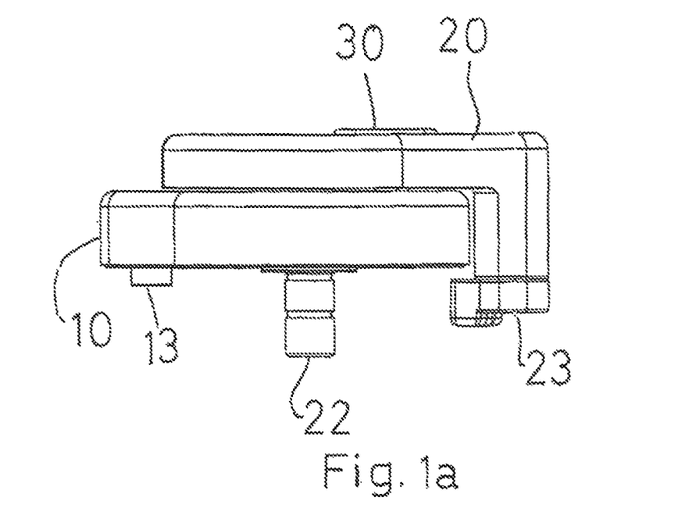
FIG. 1a shows a side view according to FIG. 1.

FIG. 1a shows a side view of an adjusting device 1 according to FIG. 1. The first element 10 with the bore 13 is arranged below the second element 20 with the bore 23. The actuating element 30 can be seen on the upper surface. On the bottom side, below the first element, the pivot axis 22 protrudes in the form of a journal. The rails or components can be secured on the journal 22. The second fastening point for example for the orthesis rails is then in each case the accommodating bore 13, 23 of the first or second element 10, 20 such that torques are able to be transferred.

Figure 2:
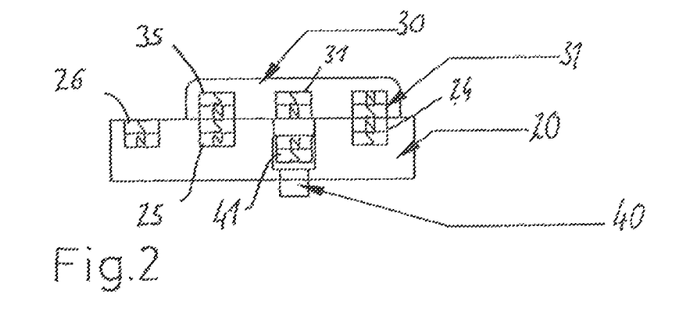
FIG. 2 shows a sectional representation an element in the locked state.

FIG. 2 shows a part view of a schematic sectional representation of the second element 20. Normally, the second element lies on the outer side of the adjusting device such that the actuating element 30 lies on the outer side of the adjusting device 1 and is consequently easily accessible. In the embodiment according to FIG. 2, the actuating element 30 is realized as a sliding switch which is arranged on the upper surface of the second element 20. Two actuating magnets 31 with opposite magnetic polarity are arranged inside the sliding switch 30, the right-hand actuating magnet 31 has north/south magnetic polarity, the central actuating magnet 31 has south/north magnetic polarity and the left-hand holding magnet 35 also has a south/north magnetic polarity.

Three holding magnets 24, 25, 26 are arranged in the second element 2, their magnetic polarity is aligned such that they have an attracting effect on the two outer magnets 31, 35 of the actuating element 30. This means that the magnetic polarity of the holding magnets 24, 25 is equidirectional to the magnetic polarity of the right-hand actuating magnet 31 and of the left-hand holding magnet 35. The right-hand actuating magnet 31 and the holding magnet 35 are positioned in a manner corresponding to the holding magnets 24, 25. Corresponding to the central actuating magnet 31 of the actuating element 30, a locking element 40 is arranged in the form of a slidingly mounted bolt in the second element 20. The locking element 40 protrudes on the underside of the second element 20 such that it is able to engage in a latching device (not shown) in the first element 10. In order to be able to exert a force component downward in the direction of the second element 10, a locking magnet 41 is arranged in the locking element 40, the magnetic polarity of which locking magnet is selected such that a repelling movement is exerted by the central actuating magnet 31. In the exemplary embodiment shown, the two magnetic north poles face one another.

Figure 3:
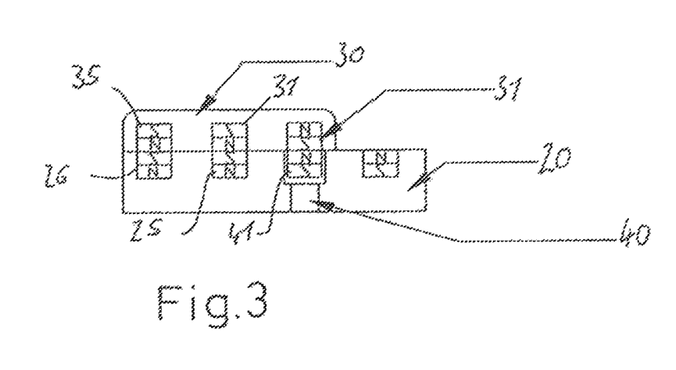
FIG. 3 shows a sectional representation according to FIG. 2 in the unlocked state.

FIG. 3 shows the embodiment in the unlocked state, the actuating element 30 is displaced to the left such that the left-hand holding magnet 35 comes to rest on the outside holding magnet 26. As a result of the equidirectional magnetic polarity, the two holding magnets 26, 36 exert an attracting force on one another. By means of the displacement into the unlocking position, the central actuating magnet 31 is moved to coincide with the holding magnet 25, which is arranged on the left next to the locking element 40, and is held there securely equally as a result of the equidirectional magnetic polarity. By means of the displacement, the right-hand actuating magnet 31 is moved to coincide with the locking element 40 and the locking magnet 41, in this case too, as a result of the equidirectional magnetic polarity of the magnets 31, 41, the two magnets attract and consequently the locking element 40 is also displaced in the direction of the actuating magnet 31. As a result, it is possible to move the locking element 40 out of the locking position according to FIG. 2 into the release position according to FIG. 3 such that the two elements 10, 20 are able to be rotated in a freely pivotable manner about the pivot, axis 22.

Figure 4:
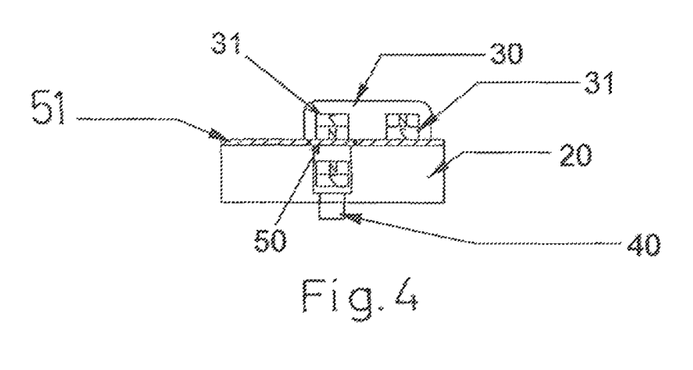
FIG. 4 shows a variant of the invention in the locked state.
Figure 5:
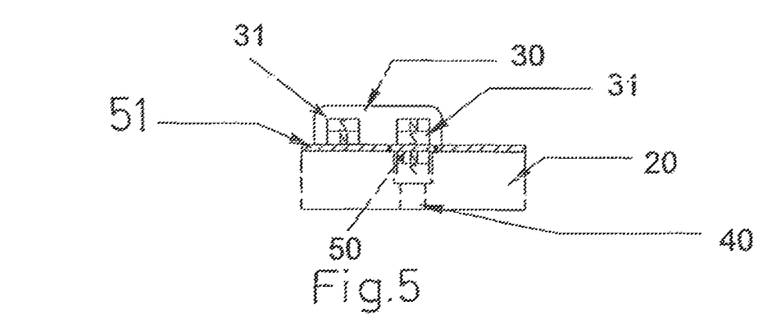
FIG. 5 shows an element according to FIG. 4 in the unlocked state.

One variant of the invention is shown in FIGS. 4 and 5. Only two actuating magnets 31 are arranged in the actuating element 30 instead of three magnets in the actuating element 30, the magnetic polarity of the two actuating magnets 31 is different. A coating 51 which is magnetizable is applied on the upper surface of she second element 20 or a wall 51 which is magnetizable is arranged on the upper surface of the second element 20. As a result, it is possible for the actuating element 30 to adhere to the wall 51. The wall 51 can extend over the entire surface of the second element 20, as an alternative to this it is possible to arrange a magnetizable material in regions on the surface of the second element 20. A non-magnetizable layer 50, which can be realized, for example, as a sliding layer, is arranged in the region of the locking magnet 41. By means of the interruption in the magnetizable layer 51 it is possible for opposite polarities to be able to be realized on both sides of the neutral layer 50 such that the actuating element 30 is held in each position by means of at least one actuating magnet 31 on the second element 20.

FIG. 4 shows the locking state where the locking element 40 projects beyond the underside of the second element 20. The locking element 40 is held in the locking position as a result of the magnetic polarity of the actuating magnet 30 and of the locking magnet 41 which repel with respect to one another.

In FIG. 5 the actuating element 30 has been displaced, the actuating magnet 31 with the reverse magnetic polarity is aligned with respect to the locking element 40 and by means of the locking magnet 41 pulls the locking element 40 upward. The wall 50 serves as a stop.

The locking element 40 can be provided with a spring loading in the direction of a preferred position, either into the locking position or into the release position.

Figure 6:
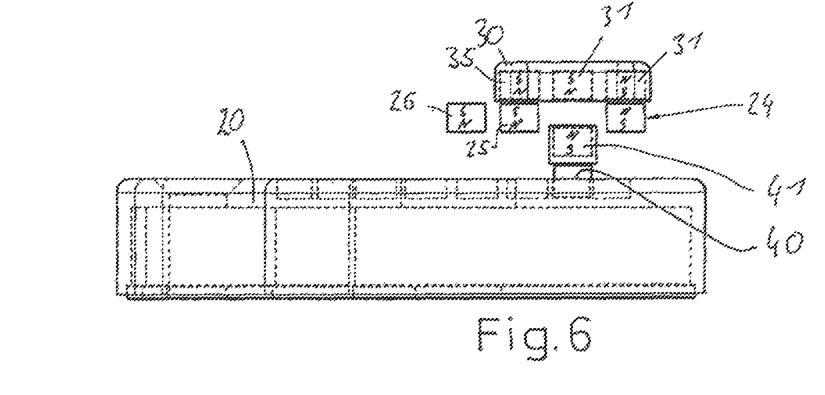
FIG. 6 shows a schematic side view of an upper part.

FIG. 6 shows a side view of a second element 20. The actuating element 30 with three magnets 31, 35 according to FIGS. 2 and 3 can be seen along with the arrangement and orientation of the locking element 40 and of the locking magnet 41 on the upper surface of the locking element 40.

Figure 7:
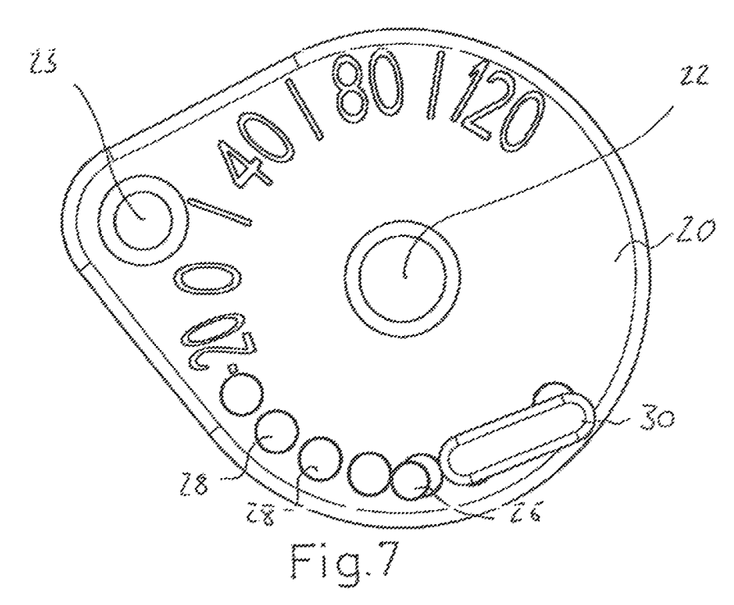
FIG. 7 shows a top view of an upper part.

A top view of she second element 20 with the rotational axis 22 and the bore 23 for the accommodation, for example, of a screw for securing the second element 20 on an orthesis rail can be seen in FIG. 7. The actuating element 30 and a holding magnet 26 can be seen on the upper surface. Together with the holding magnets 24, 25, 26 and the locking element 40, the actuating element 30 can be moved into recesses 28 on the upper surface of the element 20 by way of the locking element 40 in order to secure different stop positions of the locking element 40. As a result, it is possible to secure the pivot angle of the second element 20 in relation to the first element 10.

Figure 8:
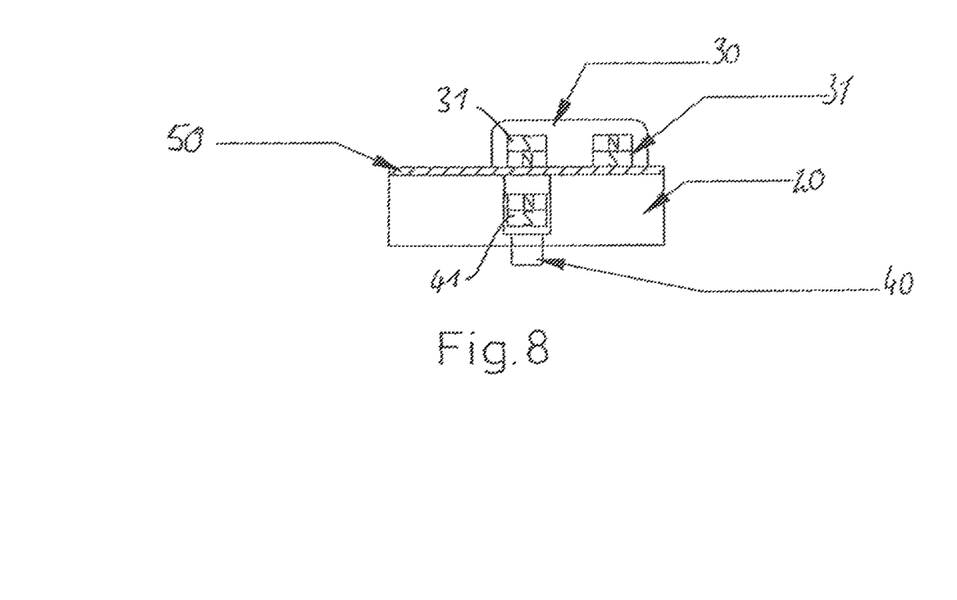
FIG. 8 shows a variant of FIG. 4.
Figure 9:
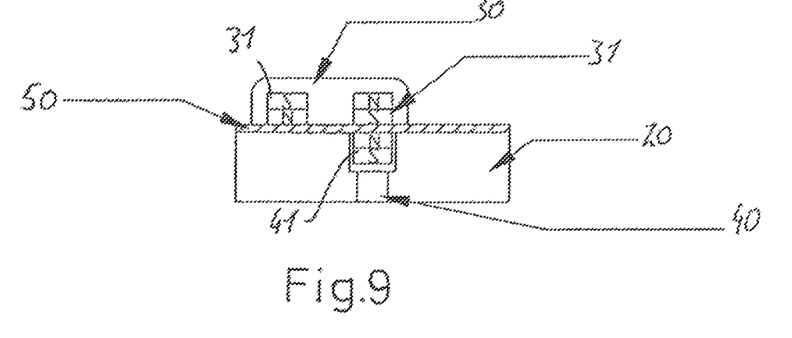
FIG. 9 shows a variant of FIG. 5.

FIGS. 8 and 9 show a variant of the embodiment according to FIGS. 4 and 5. Instead of a magnetzable layer 51, by means of which the actuating element 30 is held or additionally secured on the second element 20 by means of the actuating magnet 31, a continuous sliding layer 50 which is not magnetizable is arranged in the variant according to FIGS. 8 and 9. Insofar as the second element 20 does not consist of a magnetizable material, the actuating element 30 or the magnetic switch is held on the second element 20 by means of a guide (not shown), for example a dovetail guide, a groove guide or the like.

Figure 10:
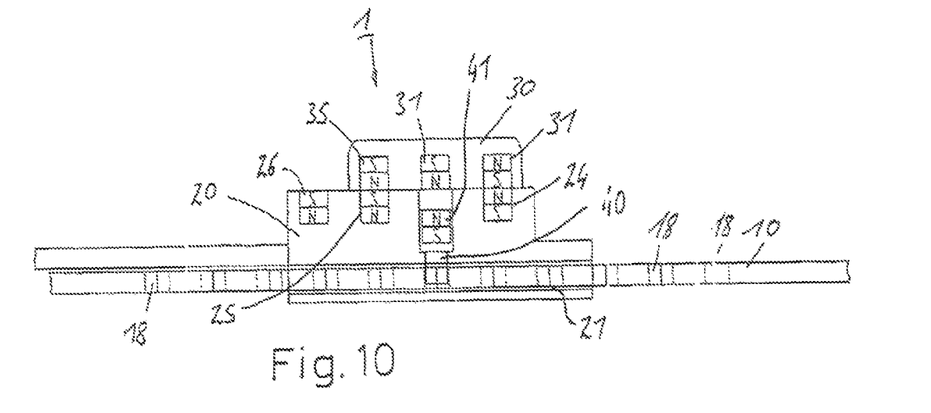
FIG. 10 shows a sectional view of a slidable variant.

FIG. 10 shows a side view of a variant of the locking device 1, where instead of a bearing arrangement about a common pivot axis the two elements 10, 20 are mounted so as to be slidable toward one another. The first element 10 is essentially realized as a flat rail with recesses 18 in which the locking element 41 is able to engage when it is situated in the locking position. A recess or guide 21 for the accommodation of the first element 10 is realized in the second element 20. The first element 10 can be slid along its longitudinal extension inside the guide 21. Coatings to facilitate the relative movement between the first element 10 and the second element 20 can be provided in the guide 21.

The design of the second element corresponds substantially to that of FIG. 2, the actuating element 30 in the form of a magnetic switch is provided with three magnets 31, 35, two of which, are realized as actuating magnets 31 and one of which, as holding magnet 35. Three holding magnets 24, 25, 26 are arranged on the surface of the second element 20, which is opposite the bottom surface of the magnetic switch 30, and are secured therein. A locking magnet 41 is arranged so as to be displaceable in a recess inside the second element 20 and, in the representation according to FIG. 10, is pressed away downward by the actuating magnet 31 as a result of the repelling magnetic polarity. As a result, the locking element 40 in the form of a journal is pressed into a recess 18 inside the rail-shaped first element 10 and locks the first element 10 in a positive locking manner against a displacement movement in relation to the second element 20 and to a component possibly arranged thereon.

Figure 11:
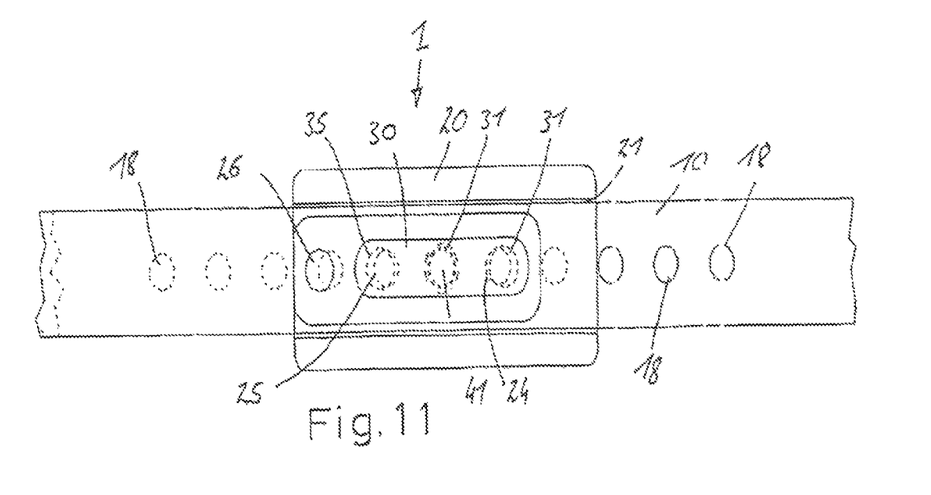
FIG. 11 shows a top view according to FIG. 10.

FIG. 11 shows a top view of the arrangement according to FIG. 10.

By means of the adjusting device 1, it is consequently possible to adjust or to lock not only elements 10, 20 which are mounted so as no be rotatable with respect to one another, but also slidable elements 10, 20. By means of the adjusting device 1, it is possible to provide permanent locking or unlocking by means of a one-time actuation of the actuating element 30 without further forces having had to be applied by the user. As soon as the actuating element 30 is situated in the unlocking position, the locking element 40 is permanently acted upon with a force which would like no move the locking element 40 out of a positive-looking locking arrangement. As soon as displacement of the locking element 40 is possible, for example in the case of a joint mechanism being relieved or the ceasing of a tensile force or a compression force where two elements 10, 20 are mounted in a slidable manner with respect to one another, the locking is released and an adjustment is able to be effected. In reverse, in the case of a corresponding position of the actuating element 30, the actuating element 30 of the actuating magnet 31 presses the locking element 40 in the direction of a recess 18 in order to bring about a positive-locking locking arrangement. As soon as the recess 30 is situated in a position which corresponds to the direction of movement of the locking element 40, the locking element 40 latches into the recess 18 and secures the two elements 10, 20 in the adjusted position with respect to one another.

The invention claimed is:

1. An adjusting device having a first element and a second element, which is mounted so as to be displaceable with respect to the first element, the first element has at least one latching device, at least one locking element, which is coupled with an actuating element, is arranged so as to be displaceable on the second element, said locking element being movable out of a release position out of engagement with the latching device into a locking position in engagement with the latching device, wherein the actuating element has at least one actuating magnet which is associated with a locking magnet which is coupled with the locking element and the locking element moves into the release position and/or locking position and/or out of the release position and/or locking position.

2. The adjusting device as claimed in claim 1, wherein the actuating element is mounted so as to be pivotable or displaceable on the adjusting device.

3. The adjusting device as claimed in claim 1, wherein the locking element is realized as a slidably mounted pin and the latching device is realized as a recess.

4. The adjusting device as claimed in claim 1, wherein the actuating magnet can have its magnetic polarity reversed or is mounted so as to be able to have its magnetic polarity reversed.

5. The adjusting device as claimed in claim 1, wherein at least one holding magnet, which holds the actuating element in the respective position on the second element, is arranged on the actuating element.

6. The adjusting device as claimed in claim 5, wherein the locking element is arranged on the second element between two holding magnets which are aligned with opposite poles and a further holding magnet with the same magnetic polarity is arranged next to the holding magnet with a magnetic polarity which deviates from the locking magnet.

7. The adjusting device as claimed in claim 5, wherein the locking element is positioned on the second element between first and second holding magnets, which are aligned with opposite poles, and a third holding magnet having a magnetic polarity opposite a magnetic polarity of the locking magnet is positioned on an opposite side of one of the first or second holding magnets having the same magnetic polarity as the third holding magnet.

8. The adjusting device as claimed in claim 1, wherein the second element is magnetizable at least in part.

9. The adjusting device as claimed in claim 1, wherein the locking element is mounted in a spring-loaded manner in the second element.

10. The adjusting device as claimed in claim 1, wherein elements are mounted in a spring-preloaded manner about a common pivot axis and in at least one pivoting direction.

11. The adjusting device as claimed in claim 1, wherein the adjusting device (1) is realized as a modular attachment part of an orthesis or prosthesis.

12. The adjusting device as claimed in claim 1, wherein at least two actuating magnets with different magnetic polarity are arranged in the actuating element.

13. The adjusting device as claimed in claim 1, wherein the locking element comprises a slidable mounted pin and the latching device comprises a recess.

14. The adjusting device as claimed in claim 1, wherein the actuating magnet has a reversible magnetic polarity or is mounted to the actuating member in opposite polarity positions.

15. The adjusting device as claimed in claim 1, further comprising at least one holding magnet positioned on the actuating element configured to releasably hold the actuating element relative to the second element.

16. The adjusting device as claimed in claim 1, wherein second element is at least partially magnetized.

17. The adjusting device as claimed in claim 1, wherein the at least one locking element has a spring-loaded mounting to the second element.

18. The adjusting device as claimed in claim 1, wherein the at least one actuating magnet includes at least two actuating magnets with different magnetic polarity.

19. An adjusting device, comprising:
a first element having at least one latching device;
a second element displaceable with respect to the first element;
at least one locking element adjustably mounted to the second element and including at least one locking magnet;
an actuating element adjustably mounted to the second element and including at least one actuating magnet;
wherein the at least one actuating magnet, when in a first position relative to the second element, moves the at least one locking element into a released position out of engagement with the at least one latching device to permit relative movement between the first and second elements, and when in a second position relative to the second element, moves the at least one locking element into a locked position in engagement with the latching device to limit relative movement between the first and second elements.

20. The adjusting device as claimed in claim 19, wherein the actuating element is pivotally mounted to the second element.

* * * * *